US012784895B2

(12) United States Patent
Abdishektaei et al.

(10) Patent No.: US 12,784,895 B2
(45) Date of Patent: Nov. 3, 2026

(54) GENERATING NATURAL LANGUAGE TEXT DESCRIBING A CHANGE BETWEEN SETS OF MEDICAL IMAGING DATA

(71) Applicant: Siemens Healthineers AG, Forchheim (DE)

(72) Inventors: Mohammad Abdishektaei, Charlottesville, VA (US); Sepehr Farhand, Malvern, PA (US); Yoshihisa Shinagawa, Downingtown, PA (US); Gerardo Hermosillo Valadez, West Chester, PA (US); Matthias Wolf, Coatesville, PA (US)

(73) Assignee: Siemens Healthineer AG, Forchheim (DE)

( * ) Notice: Subject to any disclaimer, the term of this patent is extended or adjusted under 35 U.S.C. 154(b) by 231 days.

(21) Appl. No.: 18/676,791

(22) Filed: May 29, 2024

(65) Prior Publication Data

US 2025/0062010 A1 Feb. 20, 2025

(30) Foreign Application Priority Data

Aug. 14, 2023 (EP) .................................... 23191392

(51) Int. Cl.
*G06V 10/60* (2022.01)
*G06V 10/44* (2022.01)
(Continued)

(52) U.S. Cl.
CPC ............. *G16H 30/40* (2018.01); *G06V 10/44* (2022.01); *G06V 10/60* (2022.01); *G16H 30/20* (2018.01)

(58) Field of Classification Search
CPC ........ G16H 30/40; G16H 30/20; G16H 50/70; G06V 10/60; G06V 10/44; G06V 10/757;
(Continued)

(56) References Cited

U.S. PATENT DOCUMENTS

| | | | | |
|---|---|---|---|---|
| 2019/0188848 A1* | 6/2019 | Madani | .................. | G06V 20/70 |
| 2019/0333217 A1* | 10/2019 | Bronkalla | ............. | G16H 30/40 |

(Continued)

FOREIGN PATENT DOCUMENTS

| | | | | |
|---|---|---|---|---|
| CN | 111681730 A * | 9/2020 | ............ | G06N 3/045 |

OTHER PUBLICATIONS

Anonymous; “Machine learning—Wikipedia”; Aug. 13, 2023 (Aug. 13, 2023); XP093115203.

(Continued)

*Primary Examiner* — Syed Haider

(57) ABSTRACT

A framework for generating natural language text describing a change between first medical imaging data and second medical imaging data is disclosed. Imaging data representative of the first medical imaging data and the second medical imaging data, or of a difference between the first medical imaging data and the second medical imaging data, is obtained. The imaging data is input into a first trained machine learning model to generate an image feature vector representative of the difference between the first medical imaging data and the second medical imaging data. Data representative of the image feature vector is input into a second trained machine learning model to generate the natural language text describing the change between the first medical imaging data and the second medical imaging data.

20 Claims, 7 Drawing Sheets

(51) Int. Cl.
*G16H 30/20* (2018.01)
*G16H 30/40* (2018.01)

(58) Field of Classification Search
CPC ............... G06V 10/761; G06V 10/774; G06V 2201/03; G06T 7/0016
See application file for complete search history.

(56) References Cited

U.S. PATENT DOCUMENTS

| | | | | |
|---|---|---|---|---|
| 2021/0335464 | A1 | 10/2021 | Poblenz et al. | |
| 2022/0076052 | A1* | 3/2022 | Zhang | G06F 16/3347 |
| 2023/0041804 | A1* | 2/2023 | Muller | G06T 7/0016 |

OTHER PUBLICATIONS

EP search report in EP Application No. 23191392.2, dated Jan. 26, 2024, 13 pages.

* cited by examiner

GENERATING NATURAL LANGUAGE TEXT DESCRIBING A CHANGE BETWEEN SETS OF MEDICAL IMAGING DATA

CROSS-REFERENCE TO RELATED APPLICATION

This application claims the benefit of priority from European Patent Application No. 23191392.2, filed on Aug. 14, 2023, the contents of which are incorporated by reference.

TECHNICAL FIELD

The present disclosure relates to a method and an apparatus for analyzing a change between two sets of medical imaging data.

BACKGROUND

When a patient is diagnosed with a condition using a baseline medical image, follow-up imaging is commonly recommended to monitor progression of the condition. After the follow-up image is taken, a radiologist may review the follow-up image and the baseline image, and write a report describing any progression in the condition. However, interpretation of the follow-up image and/or writing of the report is a time-consuming task.

In addition, when comparing a baseline image taken at the time of diagnosis with a follow-up image taken later, the images may include artifacts which are not relevant to the progression of the condition. For example, where the lighting or imaging angle used to capture the baseline image differs from those used to take the follow-up image, artifacts may be visible. Other irrelevant changes may be apparent in the images. This can make interpretation and/or reporting of the follow-up and baseline images difficult.

It is desirable to automate, or at least provide computer implemented assistance in, the interpretation and/or reporting of follow-up medical images.

SUMMARY

Described herein is a framework for generating natural language text describing a change between first medical imaging data and second medical imaging data. Imaging data representative of the first medical imaging data and the second medical imaging data, or of a difference between the first medical imaging data and the second medical imaging data, is obtained. The imaging data is input into a first trained machine learning model to generate an image feature vector representative of the difference between the first medical imaging data and the second medical imaging data. and inputting data representative of the image feature vector into a second trained machine learning model to generate the natural language text describing the change between the first medical imaging data and the second medical imaging data.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

Independent of the grammatical term usage, individuals with male, female or other gender identities are included within the term.

Figure 1:
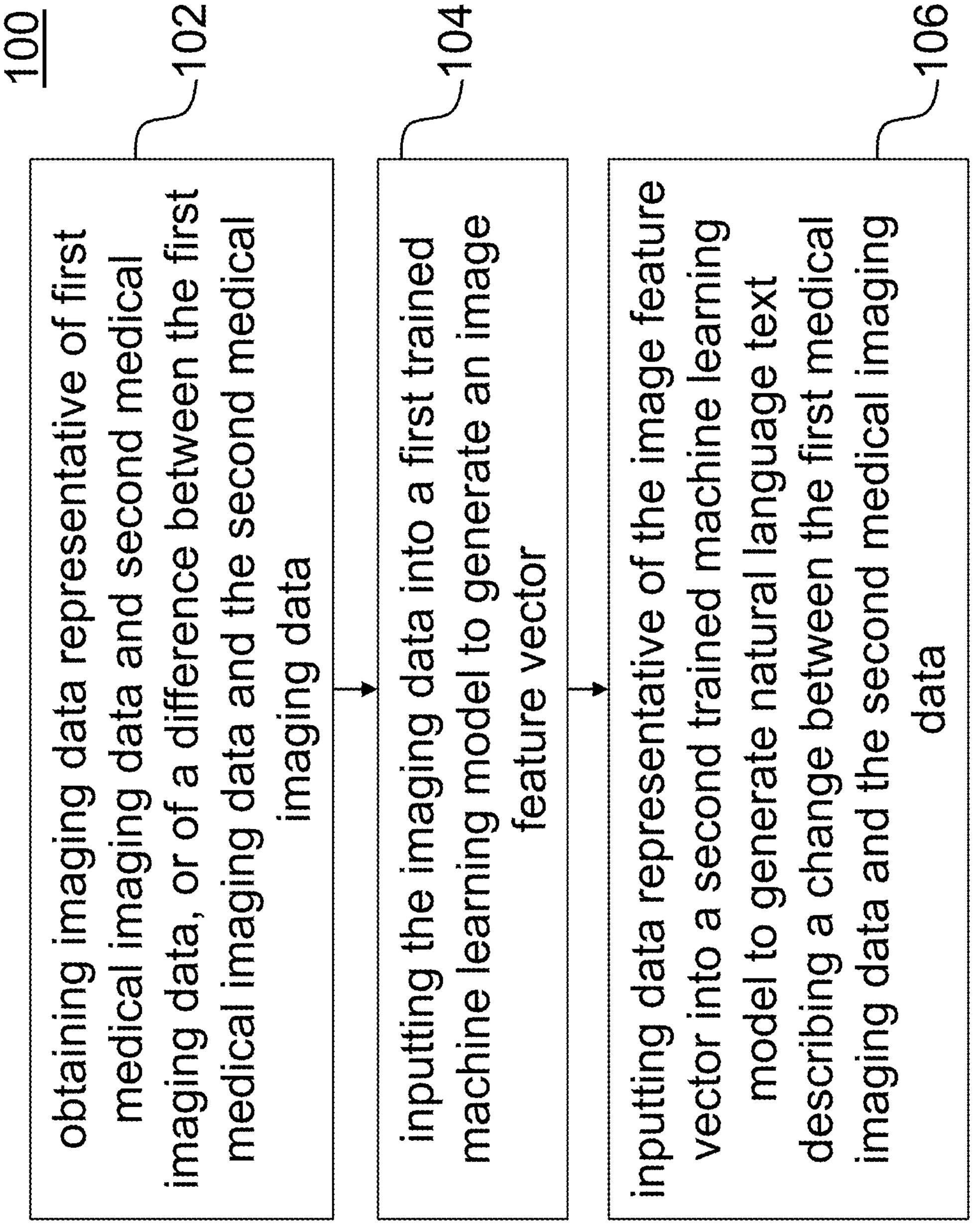
FIG. 1 is a flow diagram illustrating schematically a method for generating natural language text describing a change between first medical imaging data and second medical imaging data.

Referring to FIG. 1, there is illustrated a computer implemented method 100 for generating natural language text describing a change between first medical imaging data 302 and second medical imaging data 304.

Figure 2A:
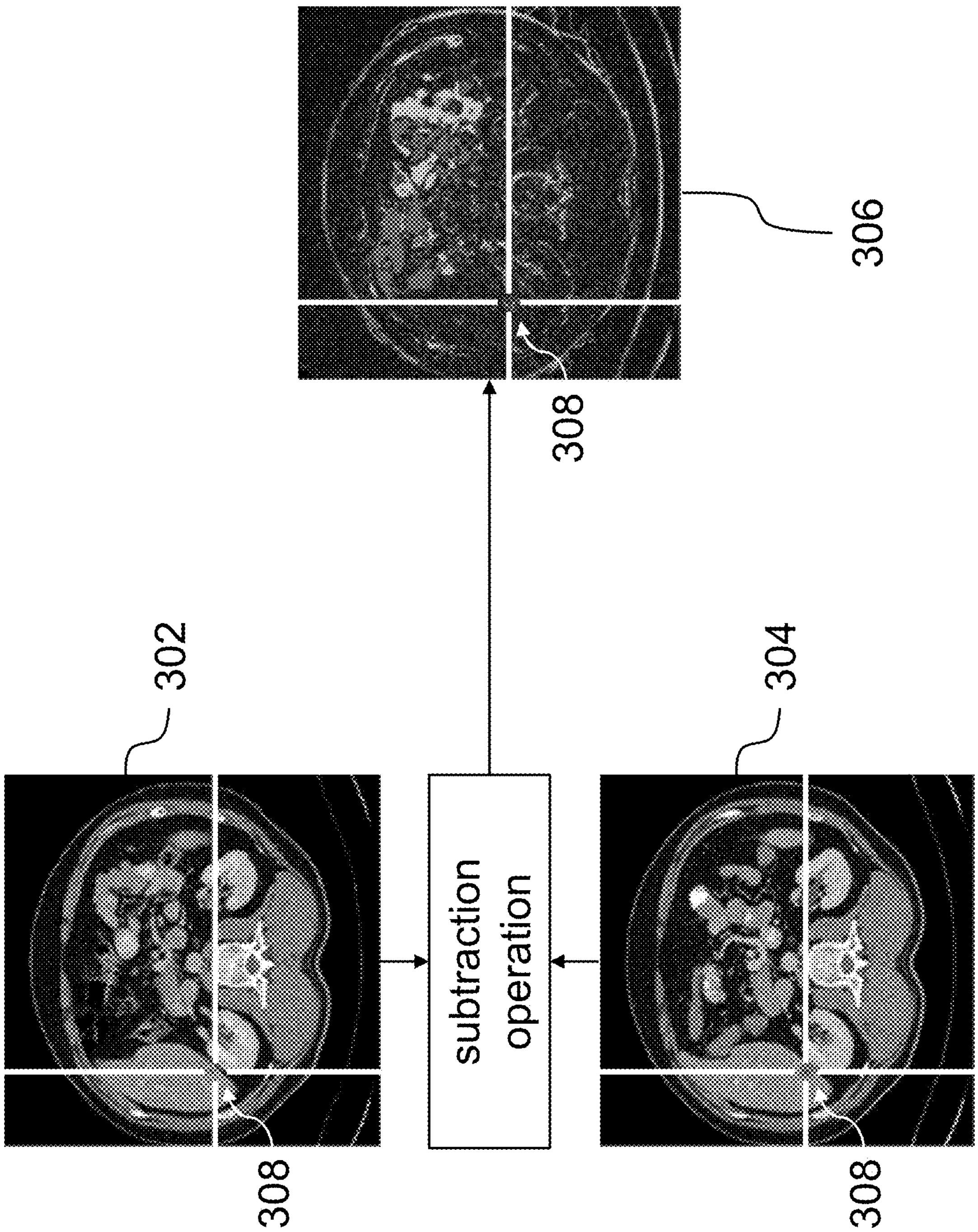
FIG. 2*a* is a flow diagram illustrating schematically a method for obtaining differential imaging data from first medical imaging data and second medical imaging data.
Figure 3:
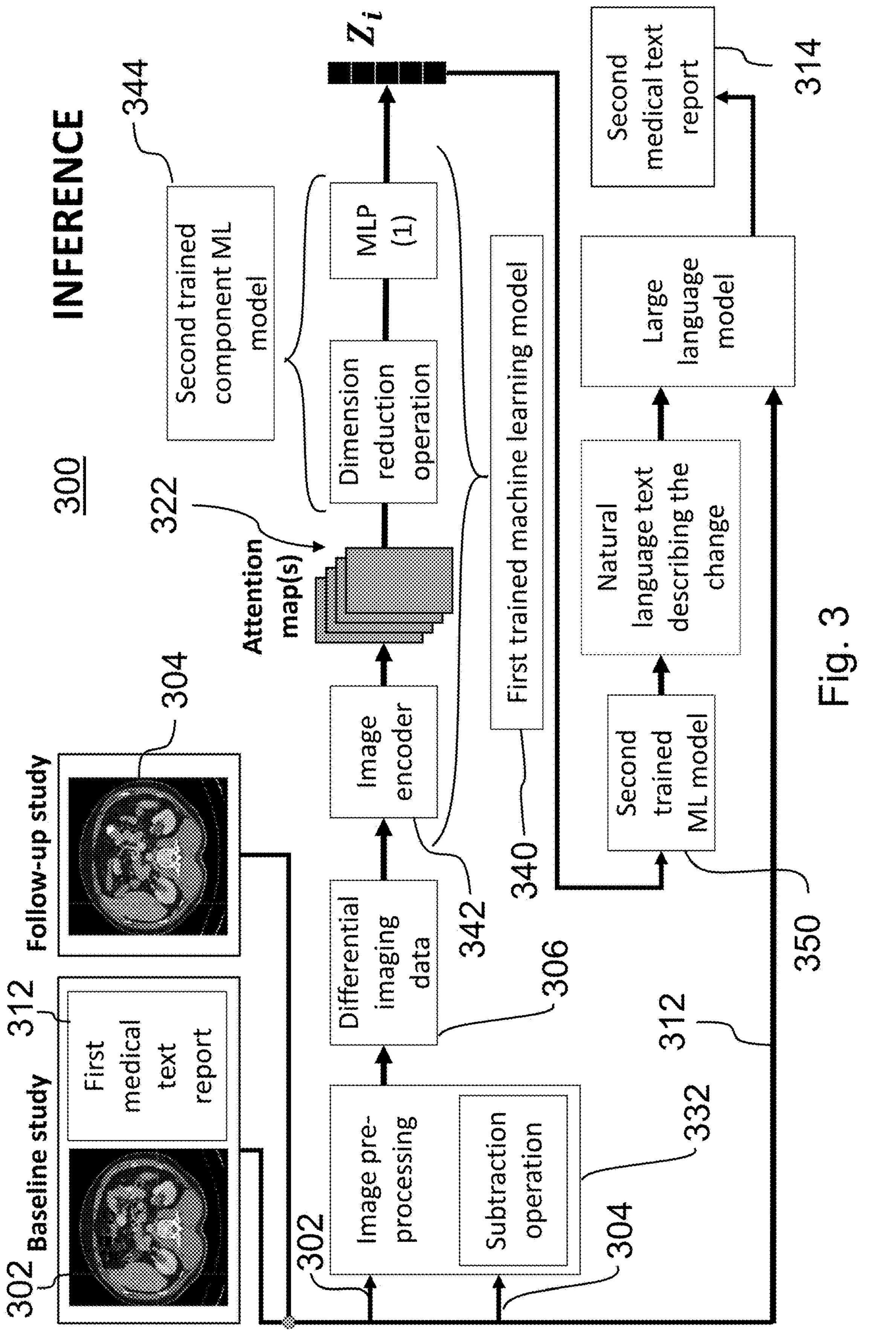
FIG. 3 is a flow diagram illustrating schematically in more detail a method according to the method illustrated in FIG. 1.

In broad overview, the method 100 comprises: in step 102, obtaining imaging data 306 representative of first medical imaging data 302 and second medical imaging data 304, or of a difference between the first medical imaging data 302 and the second medical imaging data 304 (see FIG. 2*a*); in step 104, inputting the imaging data 306 into a first trained machine learning model 340 to generate an image feature vector Zi (for example, the first trained machine learning model 340 in FIG. 3); in step 106, inputting data representative of the image feature vector Zi into a second trained machine learning model 350 to generate the natural language text describing the change between the first medical imaging data 302 and the second medical imaging data 304 (for example, see the second trained machine learning model 350 in FIG. 3).

Accordingly, natural language text describing a change between first medical imaging data 302 and second medical imaging data 304 may be generated.

By generating the image feature vector Zi based on the imaging data 306 using the first trained machine learning model 340, the image feature vector Zi can be generated that encodes features relevant to the changes between the first medical imaging data 302 and the second medical imaging data 304. Accordingly, for example, the progression of a condition of a patient depicted in the first medical imaging data 302 and the second medical imaging data 304, can be extracted and encoded into the image feature vector Zi. The second trained machine learning model 350 uses this image feature vector to generate the natural language text describing the change. Accordingly, the generated natural language text describing the change is pertinent to the relevant change (s) between the first medical imaging data and the second medical imaging data. This generated natural language text may provide for automation of the interpretation and/or reporting of the second medical image, such as a follow up image. For example, this text may represent, or be used to generate, a report for the follow-up image. Alternatively, or additionally, this generated natural language text may allow for assistance in the interpretation and/or reporting of a follow-up image to be provided. For example, a radiologist may use this generated text to guide their interpretation and/or reporting of the follow-up image.

The natural language text describing the change may be used by a medical professional in a variety of ways. For example, the medical professional may recommend a course of treatment, or decide that further follow-up imaging is required.

An example method 300 is now described in detail with reference to FIG. 3. Method 300 is a specific example of method 100 and includes the steps of method 100.

As mentioned, the method 300 comprises, in step 102, obtaining imaging data 306 representative of first medical imaging data 302 and second medical imaging data 304, or of a difference between the first medical imaging data 302 and the second medical imaging data 304. In this example, the imaging data 306 comprises differential imaging data 306 representing a difference between the first medical imaging data 302 and the second medical imaging data 304.

Each of the first medical imaging data 302 and the second medical imaging data 304 may comprise an array of elements each having a value. The elements may be pixels, each pixel having at least one value. The at least one value may correspond to or otherwise be representative of an output signal of the medical imaging technique used to generate the medical imaging data. For example, for Magnetic Resonance Imaging, the value of an element (e.g. pixel) may correspond to or represent a rate at which excited nuclei, in a region corresponding to the element, return to an equilibrium state. In some examples, each element may only have one value. However, in other examples, each element may have or otherwise be associated with multiple values. For example, the multiple values of a given element may represent the values of respective multiple signal channels. For example, each signal channel may represent a different medical imaging signal or property of the imaging subject. In some examples, the at least one value may comprise an element (e.g. pixel) intensity value. For example, an output signal from the medical imaging may be mapped onto a pixel intensity value, for example a value within a defined range of intensity values. For example, for a greyscale image, the intensity value may correspond to a value in the range 0 to 255, where 0 represents a 'black' pixel and 255 represents a 'white' pixel, for example. As another example, for example as in the case of USHORT medical image data, the intensity value may correspond to a value in the range 0 to 65536. As another example, in a color image (e.g. where different colors represent different properties of the imaging subject) each pixel may have three intensity values, e.g. one each for Red, Green, and Blue channels. It will be appreciated that other values may be used.

In some examples, the first medical imaging data 302 is for a patient and has been captured at a first time and the second medical imaging data 304 is for the patient and has been captured at a second, later, time. For example, the first medical imaging data 302 may form part of a baseline study of the patient. As shown in FIG. 3, a first medical text report 312 may be written for the baseline study. The second medical imaging data 304 may form part of a follow-up study of the patient. The follow-up study may be intended to track progression (or regression) of a medical abnormality 308, and/or to identify occurrence (or disappearance) of a medical abnormality 308 after the baseline study. In this example, the first medical imaging data 302 and the second medical imaging data 304 are for a particular region of the patient. For example, the first medical imaging data 302 and the second medical imaging data 304 may be for an abdominal region of the patient, or for a limb of the patient.

Generating natural language text describing the change where the first medical imaging data 302 is for a patient and has been captured at a first time and the second medical imaging data 304 is for the patient and has been captured at a second, later, time, enables computer implemented interpretation and/or reporting of a follow-up medical image. This in turn enables the progression of a condition of the patient to be monitored without necessarily requiring a human to analyze the first medical imaging data 302 and the second medical imaging data 304. Alternatively, or additionally, this may enable computer implemented assistance in the interpretation and/or reporting of a follow-up medical image, or the monitoring of the progression of a condition of a patient, by a medical professional.

In some examples, the method 300 comprises obtaining the first medical imaging data 302 and the second medical imaging data 304. For example, the first medical imaging data 302 and the second medical imaging data 304 may be retrieved from a storage such as a memory (see e.g. memory 604 in FIG. 6, described in more detail below). The first medical imaging data 302 may comprise a plurality of first intensity values, and the second medical imaging data 304 may comprise a plurality of corresponding, second, intensity values. That is, each of the first intensity values in the first medical imaging data 302 corresponds to a certain second intensity value in the second medical imaging data 304. Each of the first intensity values may be associated with a respective pixel location, and each of the second intensity values may be associated with one of the pixel locations, to provide this correspondence.

In this example, the method 300 comprises image pre-processing 332 of the first medical imaging data 302 and the second medical imaging data 304. For example, the image pre-processing 332 may comprise image registration. Image registration generally involves transforming the plurality of first intensity values and the plurality of second intensity values into one coordinate system. The image registration may comprise associating each of the first intensity values with its corresponding second intensity value, and the respective pixel locations may be defined during the image registration.

In some examples, the method 300 comprises, for each of the plurality of first intensity values, comparing the first intensity value with the corresponding second intensity value, to obtain a differential intensity value. In these examples, the differential imaging data 306 comprises the obtained differential intensity values. For example, as illustrated in FIG. 2*a*, comparing the first intensity value with the second intensity value may comprise performing a subtraction operation using the first intensity value and the second intensity value. For example, comparing the first intensity value with the second intensity value may comprise subtracting the second intensity value from the first intensity value, or vice versa. Subtracting the second intensity value from the first intensity value, or vice versa, may allow a computationally simple method to obtain the differential imaging data 306. In the differential imaging data 306 shown in FIGS. 2*a* and 2*b*, the regions in which the intensity value of the second medical imaging data 304 is lower than the intensity value of the first medical imaging data 302 are shown in light grey, and the regions in which the intensity value of the second medical imaging data 304 is higher than the intensity value of the first medical imaging data 302 are shown in dark grey. A medical abnormality 308 is shown on each of the first medical imaging data 302, the second medical imaging data 304, and the differential medical imaging data. The medical abnormality 308 has undergone a subtle change in appearance between the time at which the first medical imaging data 302 was captured and the time at which the second medical imaging data 304 was captured.

Figure 2B:
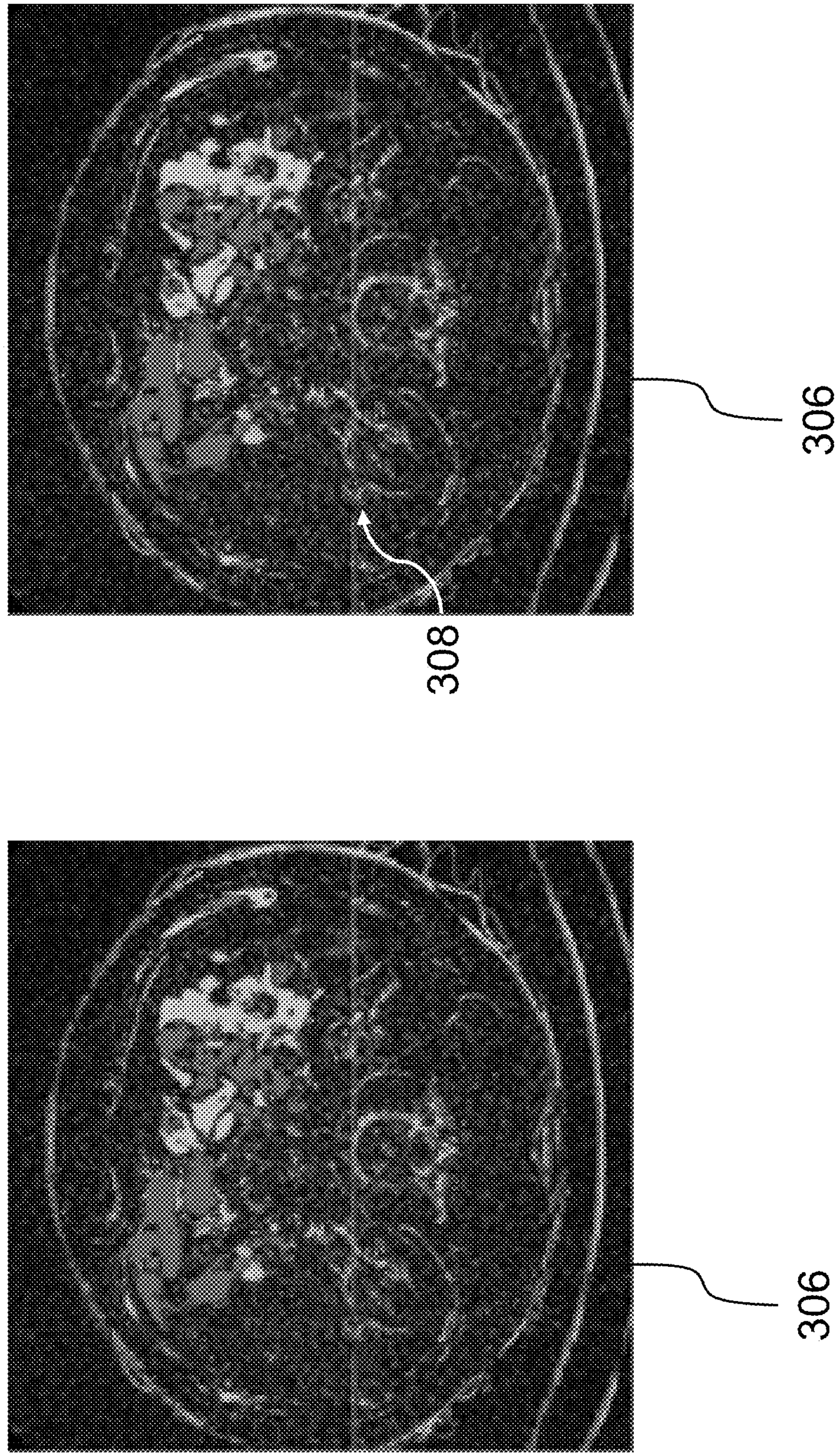
FIG. 2*b* is an illustration of the difficulties associated with identifying a medical abnormality from obtaining differential imaging data by visual inspection.

FIG. 2*b* shows two copies of the differential medical imaging data, with the position of the abnormality indicated on the second copy. As will be appreciated from the differential imaging data 306 shown in FIG. 2*b*, it may be difficult to identify a medical abnormality 308 from visual inspection of the differential imaging data 306 alone. Indeed, it may also be difficult for a computer vision system to identify a medical abnormality 308 using the differential imaging data 306 alone. Some examples described herein enable a first trained machine learning model 340 to identify a change between the first medical imaging data 302 and the second medical imaging data 304, by training the machine learning model using, in addition to medical imaging data, medical text reports associated with the medical imaging data. This will be described further with reference to FIG. 5.

As mentioned, the method 300 comprises, in step 104, inputting the imaging data 306 into a first trained machine learning model 340 to generate an image feature vector Zi representative of the difference between the first medical imaging data 302 and the second medical imaging data 304. In this example, the imaging data 306 is the differential imaging data 306, and the image feature vector Zi is representative of the differential imaging data.

In this example, the first trained machine learning model 340 has been trained to generate, based on an input of given differential imaging data representing a difference between given first medical imaging data and given second medical imaging data, an image feature vector Zi. The training process is described in further detail below with reference to FIG. 5. Any machine learning model described herein may comprise a neural network, such as a convolutional neural network or a transformer.

In this example, generating the image feature vector Zi comprises inputting the differential imaging data 306 into a first component trained machine learning model of the first trained machine learning model 340 to generate one or more attention maps 322. In this example, the first component trained machine learning model comprises an image encoder 342. The image encoder 342 has been trained to generate, based on an input of given differential imaging data 306, one or more attention maps. Through training the first trained machine learning model 340 with the further loss function 470 described below with reference to FIG. 5, the image encoder 342 may be capable of producing an attention map which indicates features of the differential imaging data 306 that may represent information pertinent to a medical text report.

Each attention map may be indicative of the extent to which a particular portion or segment of the differential imaging data 306 contributes to the encoding or a particular part of the encoding performed by the image encoder 342. For example, each attention map may relate to a different segment, or a different context, of the differential imaging data 306. For example, one or more attention maps may each highlight the particular segment or part(s) of the differential imaging data that the image encoder 342 determines corresponds to a respective particular context. For example, a particular context may be that part(s) correspond to a medical abnormality. A segment may comprise a sub-plurality of the differential intensity values. The image encoder 342 may segment the differential imaging data 306 into the attention maps according to the contribution of each particular segment, or context, to the encoding. For example, the image encoder may be configured to segment the differential imaging data 306 based on the respective locations of possible abnormalities occurring in the differential imaging data 306.

In this example, the method 300 comprises inputting data representative of the one or more attention maps 322 into a second component trained machine learning model 344 of the first trained machine learning model 340 to generate the image feature vector Zi. In this example, the second component trained machine learning model 344 has been trained to generate, based on an input of a given attention map, an image feature vector Zi.

The data representative of the one or more attention maps 322 may comprise the one or more attention maps 322. However, in this example, the method 300 comprises generating the data representative of the one or more attention maps 322 by applying a dimension reduction operation to each of the one or more attention maps 322. Applying the dimension reduction operation may reduce the number of pixels in the differential imaging data 306 and/or the amount of data used to store an attention map. The dimension reduction operation may comprise an average pooling operation. In general, a medical abnormality 308 is likely to be represented by a plurality of adjacent or nearby pixels. Therefore, applying the dimension reduction operation can reduce the number of pixels used to represent the differential imaging data 306, without substantially removing or dampening information relating to the medical abnormality 308 as represented by the pixels prior to the application of the dimension reduction operation. In some examples, the dimension reduction operation, such as average pooling, is a fixed operation applied to the pixels, in the sense that it does not itself involve applying a machine learning model to the one or more attention maps 322.

In this example, the second component machine learning model comprises a multi-layer perceptron (MLP) 1. The multi-layer perceptron has been trained to generate, based on an input of data representative of one or more given attention maps 322 (whether the dimension reduction operation has been applied to the given attention maps 322 or not), an image feature vector Zi. Generating the image feature vector Zi may comprise inputting data representative of the one or more attention maps 322 (whether the dimension reduction operation has been applied to the attention maps 322 or not) to the MLP 1 to generate the image feature vector Zi.

The image feature vector Zi may accurately represent features of the imaging data 306 that would be relevant for a medical professional analyzing the first medical imaging data 302 and the second medical imaging data 304. The way in which the first machine learning model 440 may be trained to generate an image feature vector Zi with such properties is explained below with reference to FIG. 5.

As mentioned, the method 300 comprises, at step 106, inputting data representative of the image feature vector Zi into a second trained machine learning model 350 to generate natural language text describing a change between the first medical imaging data 302 and the second medical imaging data 304.

The second trained machine learning model 350 may have been trained to generate, based on an input of given data representative of the image feature vector Zi, natural language text describing a change between the given first medical imaging data and the given second medical imaging data. The training process is described in further detail below with reference to FIG. 5.

By "describing a change", it is meant that the natural language text typically describes the change in such a way that the description of the change is comprehensible by a medical professional. Thus, the invention may enable the automatic generation of a description of a change between first medical imaging data 302 and second medical imaging data 304. The medical professional may use the description of the change to, for example, diagnose a medical condition, or recommend treatment. In any case, by generating such natural language text, the radiologist or other medical professional can understand what change(s) has/have occurred between the first medical imaging data 302 and the second medical imaging data 304, without needing to evaluate the first medical imaging data 302 or the second medical imaging data 304. Moreover, a radiologist visually inspecting the first medical imaging data 302 and the second medical imaging data 304, or the differential imaging data 306, may miss a change that has occurred. By generating natural language text describing the change according to the methods illustrated in FIGS. 1 and 3, a change between two sets of medical imaging data may allow such overlooking to be avoided.

In some examples, the change represents the occurrence or progression of a medical abnormality 308. For example, the change may represent the initial appearance or growth of a tumor between the first medical imaging data 302 and the second medical imaging data 304. In these examples, the initial appearance of a medical abnormality 308 may be identified, or the progression of the medical abnormality 308 may be tracked, by generating the natural language text describing the change. In examples in which the first medical imaging data 302 is for a patient and has been captured at a first time and the second medical imaging data 304 is for the patient and has been captured at a second, later, time, a change in the patient's condition may be monitored.

In this example, the method 300 comprises generating a second medical text report 314 associated with the second medical imaging data 304, based on a first medical text report 312 associated with the first medical imaging data 302 and the natural language text describing the change. The first medical text report 312 may describe the first medical imaging data 302 or any feature in the first medical imaging data 302. In this example, the first medical text report 312 comprises at least one sentence such as "There is a hypodense lesion in the right lobe of the liver". The second medical text report 314 may describe the second medical imaging data 304 or any feature in the second medical imaging data 304. In this example, the second medical text report 314 comprises at least one sentence such as "Again visualized is a hypodense lesion in the right lobe of the liver. There is an increase in size". The second medical text report 314, like the natural language text describing the change, may describe any change that has occurred between the first medical imaging data and the second medical imaging data. In this example, the natural language text describing the change comprises at least one sentence such as "There is an increase in the size of an hypodense lesion in the right lobe of the liver".

By generating the second medical text report 314 based on not only the natural language text describing the change but also the first medical text report 312, the first medical text report 312 may act as a guide in generating the second medical text report 314. Thus, a second medical text report 314 that focuses on changes as compared to the information described in the first medical text report can be provided.

In this example, generating the second medical text report 314 may comprise inputting the first medical text report 312 and the natural language text describing the change to a natural language processing model. In this example, the natural language processing model is a trained natural language processing machine learning model. Specifically, in this example, the trained natural language processing machine learning model is a trained large language model, such as ChatGPT or GPT-4. In this example, the trained large language model has been trained to (among other things) generate a second medical text report 314, based on an input of a given first medical text report 312, given natural language text describing the change, and a text prompt comprising an instruction to generate the second medical text report 314. For example, generating the second medical text report 314 may comprise inputting the following to the large language model:

"Based on the below baseline radiology report relating to a baseline radiology image, and the below description of changes that have occurred between the baseline radiology image and a follow-up radiology image, write a follow-up radiology report describing the follow-up radiology image.

Here is the baseline radiology report. [first medical text report 312]

Here is the description of changes that have occurred between the baseline radiology image and the follow-up radiology image. [natural language text describing the change]", or alternatively, "Here is a baseline radiology report relating to a base-line radiology image. [first medical text report 312]

Here is a description of changes that have occurred between the baseline radiology image and a follow-up radiology image. [natural language text describing the change]

Write a follow-up radiology report describing the follow-up radiology image.", or any other appropriate prompt. In some examples, the trained large language model has not been trained for the specific purpose described above, but has instead been trained for general natural language processing.

By generating the second medical text report 314 using a natural language processing model, the efficiency with which the second medical text report 314 is generated can be improved compared to a medical professional writing the second medical text report 314. By using a trained natural language processing machine learning model or a large language model to generate the second medical text report 314, the contents of the second medical text report 314 may be more pertinent to the change described in the natural language text.

Figure 4:
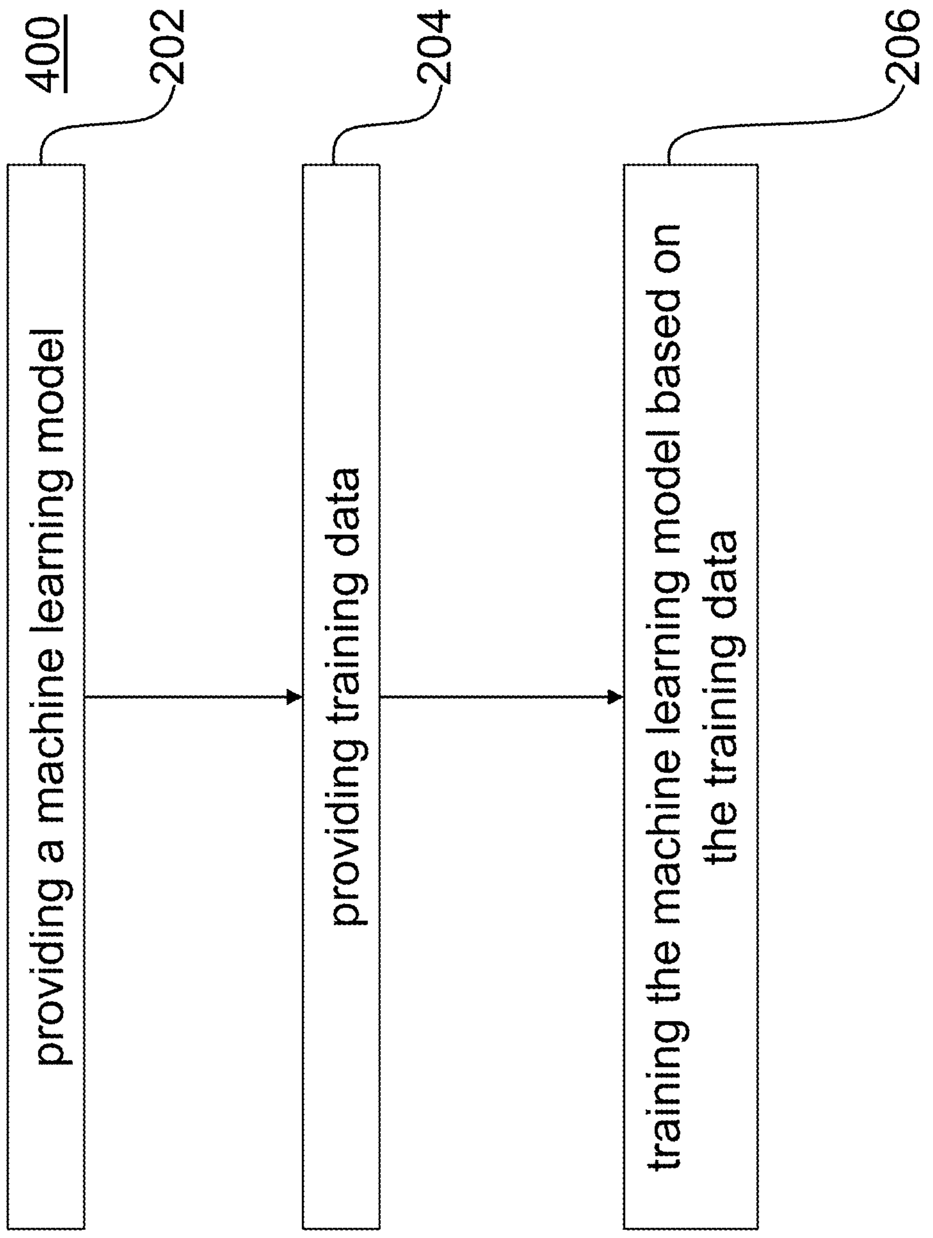
FIG. 4 is a flow diagram illustrating schematically a method for training a machine learning model to perform the method illustrated in FIG. 1.
Figure 5:
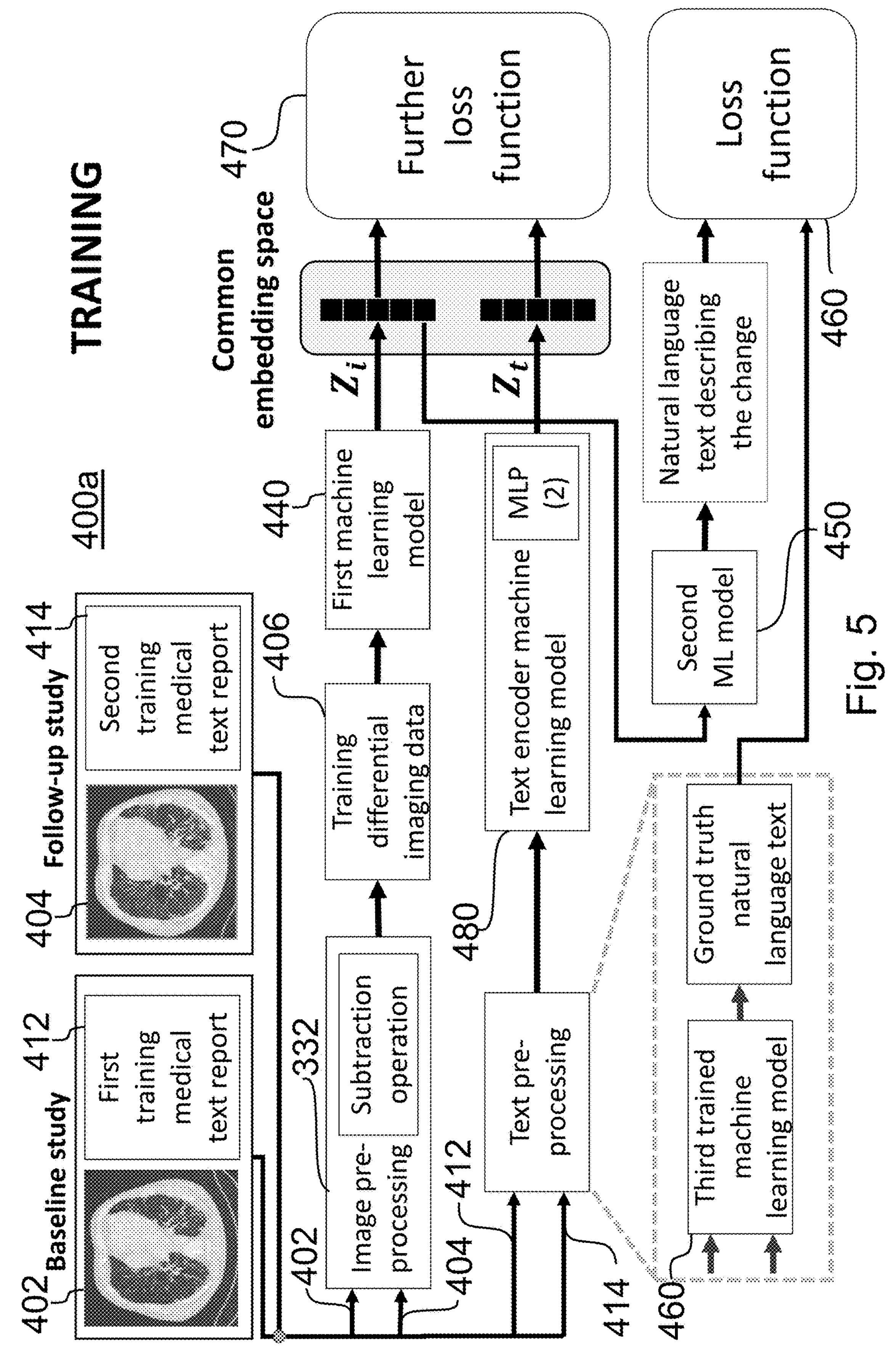
FIG. 5 is a flow diagram illustrating schematically in more detail a method according to the method illustrated in FIG. 4.

Referring to FIGS. 4 and 5, there is illustrated a computer implemented training method 400, 400*a* of training a machine learning model for generating natural language text describing a change between first medical imaging data 302 and second medical imaging data 304. The first trained machine learning model 340 and the second trained machine learning model 350 described above with reference to FIGS. 1 to 3 may be (or have been) trained according to the training method 400 outlined in FIGS. 4 and 5. Meanwhile, the trained natural language processing machine learning model (e.g. ChatGPT) may have been trained in a separate process, and may be used in the course of the training method 400 in its already trained form. The computer-implemented training method 400*a* illustrated in FIG. 5 is a specific example of the computer-implemented training method 400 illustrated in FIG. 4.

The training method 400, 400*a* comprises, in step 202, providing the machine learning model.

The machine learning model comprises (a) a first machine learning model 440 configured to generate, based on an input of given imaging data representative of given first medical imaging data and given second medical imaging data, or of a difference between the given first medical imaging data and the given second medical imaging data, an image feature vector Zi. In this example, the given imaging data is given differential imaging data representing the difference between the given first medical imaging data and the given second medical imaging data. The first machine learning model 440 may have similar architecture to or the same architecture as the first trained machine learning model 340, for example it may comprise the first component machine learning model and the second component machine-learning model. This architecture is abbreviated in FIG. 5. The machine learning model also comprises (b) a second machine learning model 450 configured to generate, based on an input of data representative of the image feature vector Zi, natural language text describing a change between the given first medical imaging data and the given second medical imaging data. The second machine learning model 450 may have similar architecture to or the same architecture as the second trained machine learning model 350.

In this example, the machine learning model comprises (c) a text encoder machine learning model. The text encoder machine learning model is configured to generate a text feature vector Zt, based on an input of data, where the data is representative of a given first medical text report associated with the given first medical imaging data and a given second medical text report associated with the given second medical imaging data. The data representative of the given first medical text report and the given second medical text report may comprise data representative of the first medical text report and data representative of the second medical text report. Additionally, or alternatively, the data representative of the given first medical text report and the given second medical text report may comprise data representative of the given natural language text describing the change.

The training method 400, 400*a* comprises, in step 204, providing training data.

The training data comprises a plurality of sets of training imaging data 406, each set of training imaging data 406 representative of first training medical imaging data 402 and second training medical imaging data 404, or of a difference between the first training medical imaging data 402 and the second training medical imaging data 404. The training data further comprises, for each set of training image data 406, ground truth natural language text describing a change between the first training medical imaging data 402 and the second training medical imaging data 404. In this example, the training imaging data is training differential imaging data representing the difference between the first training medical imaging data 402 and the second training medical imaging data 404.

In this example, providing the training data comprises generating, for each set of training differential imaging data 406, the ground truth natural language text. In this example, generating the ground truth natural language text is performed by inputting a first training medical text report 412 associated with the first training medical imaging data 402 and a second training medical text report 414 associated with the second training medical imaging data 404 into a third, trained machine learning model 460. In this case, the training data may comprise, for each set of training differential imaging data 406, the first training medical text report 412 and the second training medical text report 414. The third training machine learning model 460 may be a trained large language model. The third training machine learning model 460 may be the same as the trained large language model described above with reference to FIGS. 1 to 3 (e.g. ChatGPT or GPT-4), or it may be a different large language model. The trained large language model may have been trained to (among other things) generate the ground truth natural language text, based on an input of a given first training medical text report associated with given first training medical imaging data, a given second training medical text report associated with given second training medical imaging data, and a text prompt comprising an instruction to generate the ground truth natural language text. For example, generating the natural language text may comprise inputting the following to the large language model:

"Write a description of any differences between the following baseline and follow-up radiology reports.
Here is the baseline radiology report. [given first training medical text report] Here is the follow-up radiology report. [given second training medical text report]", or alternatively, "The following radiology reports describe respectively two medical images of the same patient, taken at different times.
Here is the first radiology report. [given first training medical text report]
Here is the second radiology report. [given second training medical text report]
Write a description of any changes that occurred between the times at which the medical images were taken.", or any other appropriate prompt.

By training the machine learning model using ground truth natural language text describing a change between the first training medical imaging data 402 and the second training medical imaging data 404, during the inference process, the second machine learning model 450 can accurately output natural language text describing the change. Inputting the first training medical text report 412 and the second medical text report 314 to the third, trained machine learning model 460 may provide an automated yet accurate way to generate the ground truth natural language text.

The training method 400, 400*a* comprises, in step 206, training the machine learning model based on the training data.

Training the machine learning model comprises training the machine learning model based on the training data so as to minimize a loss function 460 between the natural language text generated for the sets of training imaging data 406 by the machine learning model and the corresponding ground truth natural language text for the sets of training imaging data 406. As stated above, in this example, the training imaging data 406 is training differential imaging data 406.

Minimizing the loss function 460 may comprise reducing a distance in a change-description embedding space between a change-description text feature vector and a ground truth text feature vector. The change-description text feature vector is a vector representation in the change-description embedding space of the natural language text generated for a given set of training differential imaging data 406. The ground truth text feature vector is a vector representation in the change-description embedding space of the ground truth natural language text. For example, the loss function 460 may comprise a term which decreases as this distance decreases. Any distance referred to herein may comprise a Euclidean distance or a cosine distance, for example.

In this example, the training method 400*a* comprises training the machine learning model based on the training data so as to minimize a further loss function 470 between: the text feature vectors Zt generated for the first 412 and second 414 training medical text reports by the text encoder machine learning model 480, and the image feature vectors Zi generated for the corresponding sets of training differential imaging data 406 by the first machine learning model 440.

As mentioned above, the text encoder machine learning model 480 is configured to generate a text feature vector Zt. In this example, the text feature vector Zt is generated by inputting the first training medical text report 412 and the second training medical text report 414 to the third trained machine learning model 460 to generate natural language text. This natural language text may be identical to the ground truth natural language text described above. Then, the natural language text is input to the text encoder machine learning model 480. The text encoder machine learning model 480 may include a multi-layer perceptron (MLP) 2. The text encoder machine learning model 480 then generates, using the MLP 2, the text feature vector Zt. The text feature vectors Zt and the image feature vectors Zi may be represented in a common embedding space. The common embedding space may be the same as the change-description embedding space, or it may be different.

In some examples, minimizing the further loss function 470 may comprise reducing a distance in the common embedding space between an image feature vector Zi generated for a given set of the plurality of sets of training differential imaging data 406 and a text feature vector Zt generated for the given set. That is, the further loss function 470 may tend to attract an image feature vector Zi to the text feature vector Zt generated for the same set of training differential imaging data 406 in the common embedding space.

The further loss function 470 typically has the effect that during performance of the method 300 of FIGS. 1 to 3 (i.e. during inference), the image feature vector Zi generated by the first trained machine learning model 340 captures the features that would be considered relevant when writing the natural language text describing the change between the first medical imaging data 302 and the second medical imaging data 304. This is because, by virtue of the training using the further loss function 470, the first machine learning model 440 is trained to generate an image feature vector Zi that is close to the text feature vector Zt in the common embedding space, regardless of the contents of the training data of the set. Where the text feature vector Zt is generated using the natural language text generated from the first training medical imaging data 402 and the second training medical imaging data 404, the image feature vector Zi effectively represents the same information by nature of the further loss function. The same applies to the one or more attention maps 322.

In some examples, the further loss function 470 is a contrastive loss function 460. Minimizing the contrastive loss function 460 comprises, in addition to the above property of the further loss function, increasing a distance in the common embedding space between an image Zi or text feature vector Zt generated for one set of the plurality of sets of training differential imaging data 406, and an image Zi or text feature vector Zt generated for another set of the plurality of sets of training differential imaging data 406. That is, the contrastive loss function 460 tends to separate feature vectors belonging to different sets from one another. The contrastive loss function typically has a functional form:

$$\max S(Zi_{1d}, Zt_{1d}) + S(Zi_{2d}, Zt_{2d})$$

-continued $$\min S(Zi_{1d}, Zt_{2d}) + S(Zi_{2d}, Zt_{1d})$$

where S(x,y) is a function whose value decreases as the distance between x and y increases, 1d is a first set of the plurality of sets of training data, and 2d is a second set of the plurality of sets of training data different from the first set.

The contrastive loss function 460 thus typically has the effect that the image feature vector Zi generated for one set of differential imaging data 306 (during the inference stage i.e. the methods illustrated in FIGS. 1 and 3) is dissimilar from the image feature vector Zi generated for another set of differential imaging data 306. This typically has the effect that the natural language text describing the change that is generated by the second trained machine learning model 350 is also dissimilar for two different sets of differential imaging data 306. This may help to generate more accurate natural language text describing the change, because it typically reduces the likelihood of generating the same natural language text describing the change for two manifestly different sets of differential imaging data 306, for example two sets of differential imaging data 306 showing different medical abnormalities.

The training method 400, 400*a* may comprise training the machine learning model by applying the loss function 460 and the further loss function 470 alternately to the training data. For example, in a first stage, the first machine learning model 440 and the text encoder machine learning model 480 may process the training data to update parameters of each of the first machine learning model 440 and the text encoder machine learning model 480. In the first stage, the parameters of the second machine learning model 450 may be frozen; that is to say that they are not updated during the first stage. In a second stage, the second machine learning model 450 may process the training data to update the parameters of the second machine learning model 450. In the second stage, the parameters of the first machine learning model 440 and the text encoder machine learning model 480 may be frozen; that is to say that they are not updated during the second stage. The first stage and the second stage may be repeated alternately and iteratively until each of the first machine learning model 440, the text encoder machine learning model 480, and the second machine learning model 480 have been trained. The parameters of the third trained machine learning model 460 may be generally held fixed during both the first stage and the second stage, as the third trained machine learning model 460 has already been trained. The machine learning model may process each set of training data in this two-stage manner.

Figure 6:
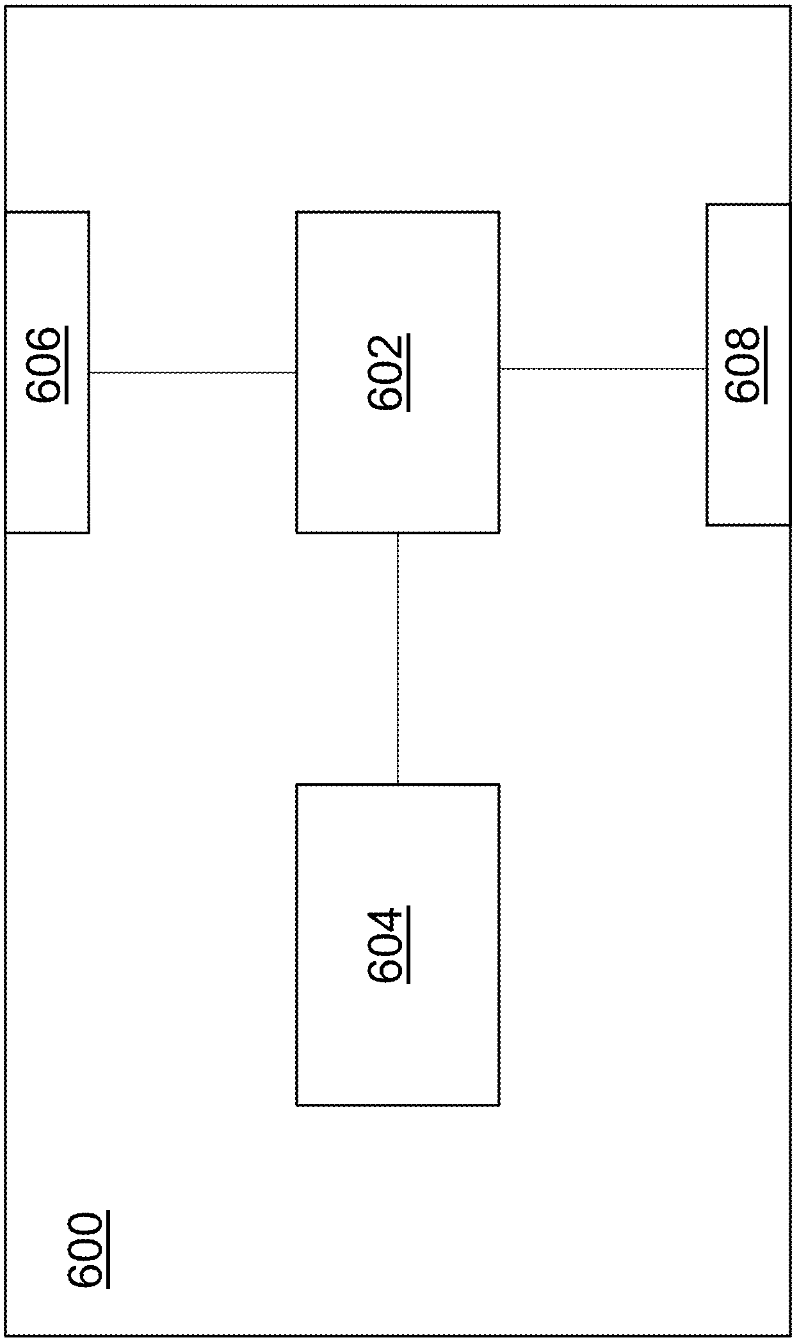
FIG. 6 is a diagram illustrating schematically an apparatus according to an example.

Referring to FIG. 6, there is illustrated an apparatus 600 according to an example. The apparatus 600 comprises an input interface 606, an output interface 608, a processor 602, and a non-transitory memory device 604. The processor 602 and the non-transitory memory device 604 may be configured to perform the method 100, 300 or the training method 400, 400*a* according to any one of the examples described above with reference to FIGS. 1 to 5. The memory may store instructions or computer readable program code which, when executed by machine or the processor 602 cause the processor 602 to perform the method 100, 300 according to any one of the examples described above with reference to FIGS. 1 to 3, and/or the training method 400, 400*a* according to any one of the examples described above with reference to FIGS. 4 to 5. The instructions may be stored on any computer readable medium, for example any non-transitory computer readable medium.

For example, the input interface 606 may receive imaging data 306, the processor 602 may implement the method 300 described above with reference to FIGS. 1 to 3 to generate the natural language text describing the change, and the processor 602 may output, via the output interface 608, the natural language text describing the change, or the second medical text report 314. In some examples, the natural language text describing the change may be transmitted to a structured storage (not shown) so that the output data is stored in the structured storage. In some examples, the natural language text describing the change, or the second medical text report 314, may be transmitted to a display device (not shown) to allow a user to review the output data. In some examples, the output data may be stored, alternatively or additionally, in the memory 604.

As another example, alternatively or additionally, the input interface 606 may receive the training data, the processor 608 may implement training of the machine learning model as described above with reference to FIGS. 4 and 5, and the processor 602 may output, via the output interface 608, the trained machine learning model or data representing the trained machine learning model. In some examples, the trained machine learning model or data representing the trained machine learning model may be stored in an external storage (not shown) or transmitted to another computer (not shown) for use by the other computer (not shown) to perform the method 300 according to any one of the examples described above with reference to FIGS. 1 to 3. In some examples, the trained machine learning model or data representing the trained machine learning model may be alternatively or additionally stored in the memory 604 or another local storage of the apparatus 600, for example for use by the apparatus 600 in implementing the method 300 according to any one of the examples described above with reference to FIGS. 1 to 3.

The apparatus 600 may be implemented as a processing system and/or a computer. It will be appreciated that the methods according to any one of the examples described above with reference to FIGS. 1 to 5 are computer implemented methods, and that these methods may be implemented by the apparatus 600.

Although in some of the above examples the imaging data is differential imaging data representing a difference between first medical imaging data and second medical imaging data, it should be understood that in other examples the imaging data may instead be representative of the first medical imaging data and the second medical imaging data. For example, obtaining the imaging data may comprise concatenating the first medical imaging data and the second medical imaging data. The method may then comprise, instead of inputting the differential imaging data into the first trained machine learning model, inputting the concatenated imaging data into the first trained machine learning model. The first trained machine learning model, by virtue of the training using the further loss function, is nevertheless capable of generating an image feature vector representative of the difference between the first medical imaging data and the second medical imaging data.

This equally applies to the training imaging data; that is to say that instead of the training method 400, 400*a* using training differential imaging data representing the difference between first training medical imaging data and second training medical imaging data, the method may use training imaging data representative of the first training medical imaging data and the second training medical imaging data. For example, each set of training imaging data may comprise a concatenation of the first training medical imaging data and the second training medical imaging data.

According to a first aspect of the present framework, there is provided a computer-implemented method for generating natural language text describing a change between first medical imaging data and second medical imaging data, the method comprising: obtaining imaging data representative of the first medical imaging data and the second medical imaging data, or of a difference between the first medical imaging data and the second medical imaging data; inputting the imaging data into a first trained machine learning model to generate an image feature vector representative of the difference between the first medical imaging data and the second medical imaging data; and inputting data representative of the image feature vector into a second trained machine learning model to generate the natural language text describing the change between the first medical imaging data and the second medical imaging data.

Optionally, the first trained machine learning model has been trained to generate, based on an input of given differential imaging data representing a difference between given first medical imaging data and given second medical imaging data, an image feature vector.

Optionally, the second trained machine learning model has been trained to generate, based on an input of given data representative of the image feature vector, natural language text describing a change between the given first medical imaging data and the given second medical imaging data.

Optionally, the method comprises generating a second medical text report associated with the second medical imaging data, based on a first medical text report associated with the first medical imaging data and the natural language text describing the change.

Optionally, generating the second medical text report comprises inputting the first medical text report and the natural language text describing the change to a natural language processing model.

Optionally, the natural language processing model is a trained natural language processing machine learning model.

Optionally, the trained natural language processing machine learning model is a trained large language model.

Optionally, the trained large language model has been trained to generate a second medical text report, based on an input of a given first medical text report, given natural language text describing the change, and a text prompt comprising an instruction to generate the second medical text report.

Optionally, the method comprises transmitting the natural language text describing the change and/or the second medical text report to a storage device for storage at the storage device.

Optionally, the method comprises transmitting the natural language text describing the change and/or the second medical text report to a display device for display on the display device.

Optionally, the first medical imaging data is for a patient and has been captured at a first time and the second medical imaging data is for the patient and has been captured at a second, later, time.

Optionally, the first medical imaging data and the second medical imaging data are for a particular region of the patient.

Optionally, the change represents the occurrence, progression, regression, or disappearance of a medical abnormality.

Optionally, the method comprises: obtaining the first medical imaging data and the second medical imaging data, the first medical imaging data comprising a plurality of first intensity values and the second medical imaging data comprising a plurality of corresponding, second, intensity values; and for each of the plurality of first intensity values, comparing the first intensity value with the corresponding second intensity value, to obtain a differential intensity value, wherein the imaging data comprises the obtained differential intensity values.

Optionally, comparing the first intensity value with the second intensity value comprises performing a subtraction operation using the first intensity value and the second intensity value.

Optionally, the method comprises: prior to comparing the first intensity values with the second intensity values, registering the first medical imaging data with the second medical imaging data by transforming the plurality of first intensity values and the plurality of second intensity values into one coordinate system.

Optionally, generating the image feature vector comprises: inputting the imaging data into a first component trained machine learning model of the first trained machine learning model to generate one or more attention maps; and inputting data representative of the one or more attention maps into a second component trained machine learning model of the first trained machine learning model to generate the image feature vector.

Optionally, the method comprises generating the data representative of the one or more attention maps by applying a dimension reduction operation to each of the one or more attention maps.

Optionally, the one or more attention maps comprise a plurality of attention maps, and each attention map relates to a different segment of the imaging data.

According to a second aspect of the present framework, there is provided a computer implemented training method of training a machine learning model for generating natural language text describing a change between first medical imaging data and second medical imaging data, the method comprising: providing the machine learning model, the machine learning model comprising: (a) a first machine learning model configured to generate, based on an input of given imaging data representative of given first medical imaging data and given second medical imaging data, or of a difference between the given first medical imaging data and the given second medical imaging data, an image feature vector, and (b) a second machine learning model configured to generate, based on an input of data representative of the image feature vector, natural language text describing a change between the given first medical imaging data and the given second medical imaging data; providing training data comprising a plurality of sets of training imaging data, each set of training imaging data representative of first training medical imaging data and second training medical imaging data, or of a difference between the first training medical imaging data and the second training medical imaging data, the training data further comprising, for each set of training imaging data, ground truth natural language text describing a change between the first training medical imaging data and the second training medical imaging data; and training the machine learning model based on the training data so as to minimize a loss function between the natural language text generated for the sets of training imaging data by the machine learning model and the corresponding ground truth natural language text for the sets of training imaging data.

Optionally, providing the training data comprises generating, for each set of training imaging data, the ground truth natural language text, by inputting a first training medical text report associated with the first training medical imaging data and a second training medical text report associated with the second training medical imaging data, into a third, trained machine learning model.

Optionally, the third trained machine learning model is a trained large language model.

Optionally, the trained large language model has been trained to generate ground truth natural language text, based on an input of a given first training medical text report associated with given first training medical imaging data, a given second training medical text report associated with given second training medical imaging data, and a text prompt comprising an instruction to generate the ground truth natural language text.

Optionally, the training data comprises, for each set of training imaging data, training data representative of the first training medical text report and the second training medical text report; the machine learning model comprises (c) a text encoder machine learning model configured to generate, based on an input of given data representative of: a given first medical text report associated with the given first medical imaging data and a given second medical text report associated with the given second medical imaging data, a text feature vector; and the method comprises training the machine learning model based on the training data so as to minimize a further loss function between: the text feature vectors generated for the first and second training medical text reports by the text encoder machine learning model, and the image feature vectors generated for the corresponding sets of training imaging data by the first machine learning model.

Optionally, the further loss function is a contrastive loss function.

Optionally, minimizing the contrastive loss function comprises: reducing a distance in the common embedding space between: an image feature vector generated for a given set of the plurality of sets of training imaging data, and a text feature vector generated for the given set; and/or increasing a distance in the common embedding space between: one of: an image feature vector generated for a first set of the plurality of sets of training imaging data and a text feature vector generated for the first set, and one of: an image feature vector generated for a second set of the plurality of sets of training imaging data and a text feature vector generated for the second set.

According to a third aspect of the present framework, there is provided apparatus configured to perform the method according to the first aspect and/or the second aspect.

Optionally, the apparatus comprises the storage device and/or the display device.

According to a fourth aspect of the present framework, there is provided a computer program which, when executed by a computer, causes the computer to perform the method according to the first aspect and/or the second aspect.

The foregoing examples have been provided merely for the purpose of explanation and are in no way to be construed as limiting of the present framework disclosed herein. While the invention has been described with reference to various embodiments, it is understood that the words, which have been used herein, are words of description and illustration, rather than words of limitation. Further, although the invention has been described herein with reference to particular means, materials, and embodiments, the invention is not intended to be limited to the particulars disclosed herein, rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

What is claimed is:

1. A computer-implemented method for generating natural language text describing a change between first medical imaging data and second medical imaging data, the method comprising:
- obtaining imaging data representative of the first medical imaging data and the second medical imaging data, or of a difference between the first medical imaging data and the second medical imaging data;
- inputting the imaging data into a first trained machine learning model to generate an image feature vector representative of the difference between the first medical imaging data and the second medical imaging data, including
  - inputting the imaging data into a first component trained machine learning model of the first trained machine learning model to generate one or more attention maps, and
  - inputting data representative of the one or more attention maps into a second component trained machine learning model of the first trained machine learning model to generate the image feature vector; and
- inputting data representative of the image feature vector into a second trained machine learning model to generate the natural language text including at least one sentence describing the change between the first medical imaging data and the second medical imaging data.

2. The method of claim 1, comprising:
- generating a second medical text report associated with the second medical imaging data based on a first medical text report associated with the first medical imaging data and the natural language text describing the change.

3. The method of claim 1, wherein the first medical imaging data is for a patient and has been captured at a first time and the second medical imaging data is for the patient and has been captured at a second, later, time.

4. The method of claim 1, wherein the change represents occurrence, progression, regression, or disappearance of a medical abnormality.

5. The method of claim 1, comprising:
- obtaining the first medical imaging data and the second medical imaging data, the first medical imaging data comprising a plurality of first intensity values and the second medical imaging data comprising a plurality of corresponding, second, intensity values; and
- for each of the plurality of first intensity values, comparing the first intensity value with the corresponding second intensity value, to obtain a differential intensity value,
- wherein the imaging data comprises the obtained differential intensity values.

6. The method of claim 5, wherein comparing the first intensity value with the second intensity value comprises performing a subtraction operation using the first intensity value and the second intensity value.

7. The method of claim 1, wherein the second component trained machine learning model of the first trained machine learning model comprises a multi-layer perceptron.

8. The method of claim 1, comprising generating the data representative of the one or more attention maps by applying a dimension reduction operation to each of the one or more attention maps.

9. The method of claim 1, wherein the one or more attention maps comprise a plurality of attention maps, and each attention map relates to a different segment of the imaging data.

10. A computer implemented training method of training a machine learning model for generating natural language text describing a change between first medical imaging data and second medical imaging data, the method comprising:
- providing the machine learning model, the machine learning model comprising:
  - (a) a first machine learning model configured to generate, based on an input of given imaging data representative of given first medical imaging data and given second medical imaging data, or of a difference between the given first medical imaging data and the given second medical imaging data, an image feature vector, and
  - (b) a second machine learning model configured to generate, based on an input of data representative of the image feature vector, natural language text including at least one sentence describing a change between the given first medical imaging data and the given second medical imaging data;
- providing training data comprising a plurality of sets of training imaging data, each set of training imaging data representative of first training medical imaging data and second training medical imaging data, or of a difference between the first training medical imaging data and the second training medical imaging data, the training data further comprising, for each set of training imaging data, ground truth natural language text describing a change between the first training medical imaging data and the second training medical imaging data, wherein providing the training data comprises generating, for each set of training imaging data, the ground truth natural language text, by inputting a first training medical text report associated with the first training medical imaging data and a second training medical text report associated with the second training medical imaging data, into a third, trained machine learning model; and
- training the machine learning model based on the training data so as to minimize a loss function between the natural language text generated for the sets of training imaging data by the machine learning model and the corresponding ground truth natural language text for the sets of training imaging data.

11. The method of claim 10, wherein the change between the given first medical imaging data and the given second medical imaging data represents occurrence, progression, regression, or disappearance of a medical abnormality.

12. The method of claim 10, wherein:
- the training data comprises, for each set of training imaging data, training data representative of the first training medical text report and the second training medical text report;
- the machine learning model comprises
  - (c) a text encoder machine learning model configured to generate, based on an input of given data representative of:
    - a given first medical text report associated with the given first medical imaging data and a given second medical text report associated with the given second medical imaging data, a text feature vector; and the method comprises training the machine learning model based on the training data.

13. The method of claim 12 wherein training the machine learning model based on the training data comprises training the machine learning model so as to minimize a further loss function between:

the text feature vectors generated for the first and second training medical text reports by the text encoder machine learning model, and the image feature vectors generated for the corresponding sets of training imaging data by the first machine learning model.

14. A system for generating natural language text describing a change between first medical imaging data and second medical imaging data:

a non-transitory memory device for storing computer readable program code; and a processor in communication with the non-transitory memory device, the processor being operative with the computer readable program code to perform steps including obtaining imaging data representative of the first medical imaging data and the second medical imaging data, or of a difference between the first medical imaging data and the second medical imaging data, inputting the imaging data into a first trained machine learning model to generate an image feature vector representative of the difference between the first medical imaging data and the second medical imaging data, including inputting the imaging data into a first component trained machine learning model of the first trained machine learning model to generate one or more attention maps, and inputting data representative of the one or more attention maps into a second component trained machine learning model of the first trained machine learning model to generate the image feature vector, and inputting data representative of the image feature vector into a second trained machine learning model to generate the natural language text including at least one sentence describing the change between the first medical imaging data and the second medical imaging data.

15. The system of claim 14, wherein the processor is operative with the computer readable program code to generate a second medical text report associated with the second medical imaging data based on a first medical text report associated with the first medical imaging data and the natural language text describing the change.

16. The system of claim 14, wherein the first medical imaging data is for a patient and has been captured at a first time and the second medical imaging data is for the patient and has been captured at a second, later, time.

17. The system of claim 14, wherein the change represents occurrence, progression, regression, or disappearance of a medical abnormality.

18. The system of claim 14, wherein the processor is operative with the computer readable program code to further perform additional steps including obtaining the first medical imaging data and the second medical imaging data, the first medical imaging data comprising a plurality of first intensity values and the second medical imaging data comprising a plurality of corresponding, second, intensity values; and for each of the plurality of first intensity values, comparing the first intensity value with the corresponding second intensity value, to obtain a differential intensity value, wherein the imaging data comprises the obtained differential intensity values.

19. The system of claim 18, wherein comparing the first intensity value with the second intensity value comprises performing a subtraction operation using the first intensity value and the second intensity value.

20. The system of claim 14 wherein the steps further comprise generating the data representative of the one or more attention maps by applying a dimension reduction operation to each of the one or more attention maps.

* * * * *